(12) United States Patent
Diaz

(10) Patent No.: US 8,690,841 B2
(45) Date of Patent: Apr. 8, 2014

(54) WOUND CARE SYSTEM

(76) Inventor: R. Gary Diaz, Highland Park, IL (US)

( * ) Notice: Subject to any disclaimer, the term of this patent is extended or adjusted under 35 U.S.C. 154(b) by 88 days.

(21) Appl. No.: 12/803,924

(22) Filed: Jul. 9, 2010

(65) Prior Publication Data
US 2011/0022008 A1 Jan. 27, 2011

Related U.S. Application Data

(60) Provisional application No. 61/270,498, filed on Jul. 9, 2009.

(51) Int. Cl.
*A61F 15/00* (2006.01)

(52) U.S. Cl.
USPC .......... 604/290; 604/304; 604/307; 604/308; 602/41; 602/42; 602/48; 602/54; 602/56

(58) Field of Classification Search
None
See application file for complete search history.

(56) References Cited

U.S. PATENT DOCUMENTS

| | | | | |
|---|---|---|---|---|
| 2,091,438 A * | 8/1937 | Morley | .......... | 604/117 |
| 2,489,675 A * | 11/1949 | Webb | .......... | 604/306 |
| 3,367,332 A * | 2/1968 | Groves | .......... | 604/290 |
| 3,530,492 A * | 9/1970 | Ferber | .......... | 604/117 |
| 4,297,995 A * | 11/1981 | Golub | .......... | 604/304 |
| 4,356,822 A * | 11/1982 | Winstead-Hall | .......... | 604/117 |
| 4,460,368 A * | 7/1984 | Allison et al. | .......... | 424/449 |
| 4,666,441 A * | 5/1987 | Andriola et al. | .......... | 424/448 |
| 4,760,847 A | 8/1988 | Vaillancourt | | |
| 4,820,279 A * | 4/1989 | Dedo | .......... | 604/290 |
| 5,066,494 A * | 11/1991 | Becher | .......... | 424/448 |
| 5,122,127 A * | 6/1992 | Stanley | .......... | 604/890.1 |
| 5,466,465 A * | 11/1995 | Royds et al. | .......... | 424/449 |
| 5,614,212 A * | 3/1997 | D'Angelo et al. | .......... | 424/449 |
| 5,744,360 A * | 4/1998 | Hu et al. | .......... | 435/366 |
| 5,827,530 A * | 10/1998 | Reed, Jr. | .......... | 424/449 |
| 5,843,018 A | 12/1998 | Shesol et al. | | |
| 6,221,384 B1 * | 4/2001 | Pagedas | .......... | 424/449 |
| 7,854,732 B2 * | 12/2010 | Massengale et al. | .......... | 604/890.1 |
| 2003/0175323 A1 * | 9/2003 | Utterberg et al. | .......... | 424/423 |

FOREIGN PATENT DOCUMENTS

WO 98/22051 5/1998

* cited by examiner

*Primary Examiner* — Jackie Ho
*Assistant Examiner* — Eric Bryant
(74) *Attorney, Agent, or Firm* — Cardinal Law Group

(57) ABSTRACT

An improved wound care system is set forth. The system includes a wound care device having a first end and a second end. A fastener, adapted to extend to a desired length to selectively attach the device at an anchor, wherein the anchor is provided on a second end of the device is also provided. The fastener is sufficiently sized and formed of a suitable material to prevent the device from moving when secured to the anchor. In an embodiment, medicine is provided in a desired treatment area of the device. The medicine can be inserted via a medicinal delivery device by inserting the medicinal delivery device up to a stop on the medicinal delivery device into the wound care device.

4 Claims, 2 Drawing Sheets

WOUND CARE SYSTEM

CROSS REFERENCE TO RELATED APPLICATIONS

This application claims priority of a provisional patent application, U.S. patent application Ser No. 61/270,498 filed Jul. 9, 2009, of the present inventor and entitled, "IMPROVED WOUND CARE DEVICE", the contents of which is incorporated herein by reference.

TECHNICAL FIELD

This invention relates to an improved wound care system, and more particularly, to an improved fastening and medicinal delivery device system.

BACKGROUND

Improvements in medical devices and related technologies can be directed to devices for treatment, procedures, evaluation, patient care, and other needs. With the ever-increasing costs associated with prolonged hospital stays, improvements have been sought to improve the healing and, consequently shorten the duration of a typical patient in the hospital. One area of particular concern for hospitals, long-term care facilities, and individuals alike is in the area of wound treatment.

Wounds can develop as a result of accidents, surgical procedures, and other factors. For example, patients who are confined to rest for extended periods of time may develop decubitus ulcers as well as other conditions related to the confinement. Decubitus ulcers, in particular, can be causes by one or more factor, such as pressure, friction, shear and moisture. Treatment of these ulcers can be further complicated where the location of the ulcers are further irritated due to, for example, incontinence.

SUMMARY OF THE INVENTION

Successful wound care involves a number of considerations. Wound care can be improved by providing, for example, wound care devices suitable for the treatment of pressure ulcers and other conditions without irritating an existing wound, area susceptible to decubitus ulcers, or other clinical considerations. Such devices are discussed, for example, in U.S. Pat. Nos. 6,892,734 and 7,000,616 to Diaz, and of common inventive entity, the disclosures of which are incorporated herein by reference.

The wound care treatment systems discussed in U.S. Pat. Nos. 6,892,734 and 7,000,616 are representative of novel wound care devices including a diaper and a pad. The diaper is designed for use on the buttocks region of a patient. The pad is designed to treat or prevent pressure sores on body parts with bony protuberances other than the buttocks, such as, for example, the head, shoulder blade and the elbow.

Additional improvements to these devices can improve the overall treatment of the wound and the patient.

Accordingly, it has been discovered that traditional fastening devices, such as conventional tapes, straps or other conventional fasteners are inadequate to provide the secure fastening desired for optimal functionality of certain wound care devices. Further, additional functionality can be provided in an improved wound care system.

An improved wound care system is set forth. The system includes a wound care device having a first end and a second end. A fastener, adapted to extend to a desired length to selectively attach the device at an anchor, wherein the anchor is provided on a second end of the device is also provided. The fastener is sufficiently sized and formed of a suitable material to prevent the device from moving when secured to the anchor.

DESCRIPTION

Figure 1:
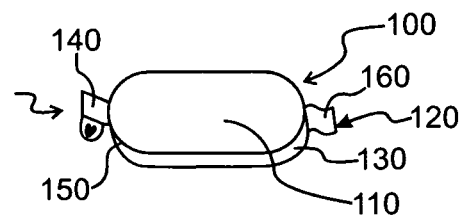
FIG. 1 illustrates an embodiment of an improved wound care system, constructed in accordance with the principles herein, wherein a fastener is in an initial rolled position.

In accordance with the principles herein, an improved wound care system, constructed in accordance with the principles herein, is shown generally at 100 in FIG. 1. The system 100 includes a suitable wound care device 110, such as, for example, a pad or diaper as discussed in U.S. Pat. Nos. 6,892, 724 and 7,000,616. A suitable anchor 120 is provided at a first end 130 of the device 110. A suitable fastener 140 is provided at a second end 150 of the device 110. This device 110 and others can be improved, in accordance with the principles herein, by incorporating an improved fastening mechanism including the suitable anchor 120 and the suitable fastener 140 used to attach the suitable wound care device 110 to patients.

The fastener 140 for the device 110 must be selected to be suitable for use on an area with bones, such as the heel, shoulders (scapula), head (cranium), knees, elbows, etc. The fastener 140 should fit to any of the standard size device 110 pads, and be capable of securing the device 110 securely in place so that a treatment area, such as the wound, is protected even during patient movement. The fastener 140 must be large and long enough to secure the pad and yet when used, not introduce an object that can become a source of irritation to the skin, such as, for example, one inch or larger. Irritations can induce new wounds, so the material chosen for the fastener 140 should be of minimum flexibility, yet sufficiently rigid to securely hold the device 110 in place.

The fastener 140 should be long enough to fit the most demanding length requirement, such as the shoulder's (scapula) requirement to fit around the patient's chest, and yet also fit a patient's elbow application. Suitable materials for the fastener 140 and anchor 120 include, but are not limited to, plastic, cloth, a fibrous material or any combination of other suitable materials. Preferably, the fastener 140 is formed of a suitable material, such that the material is capable of detachment by preformed break points, wherein the material is torn apart, or formed of a suitable material for cutting, wherein the proper length needed for the fastener 140 is determined and the fastener can be cut at the end of the needed length and secured to the anchor 12

An adhesive material can be provided on an upper surface 160 of the anchor 120 for selectively securing the fastener 140 to the anchor 120. Preferably, a suitable adhesive material is selected to permit intermittent removal and reattachment of the fastener 140 to the anchor 120.

Figure 2:
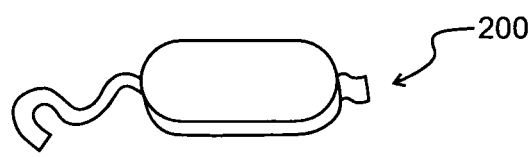
FIG. 2 illustrates an embodiment of an improved wound care system, constructed in accordance with the principles herein, wherein a fastener is in a second, unrolled position.

In order to attach the fastener 140 to the anchor 120, the fastener can be unrolled, as shown, for example, in the embodiment of FIG. 2, wherein a system constructed in accordance with the principles herein is shown generally at 200.

Figure 3:
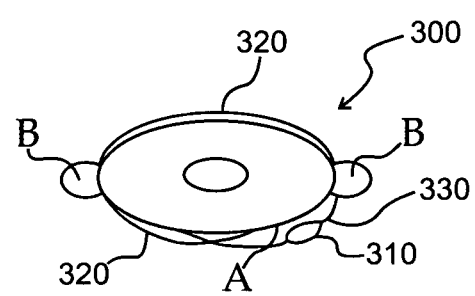
FIG. 3 illustrates an embodiment of an improved wound care system, constructed in accordance with the principles herein, wherein the improved wound care system is securely attached via a fastener and an anchor to a shoulder of a patient.

As illustrated in FIG. 3, an embodiment illustrated generally at 300 includes a wound care device 310 secured to a shoulder, indicated at A, of a patient via a fastener 320 threaded under right and left arms, indicated at B of the patient. The fastener 320 is selectively secured to an anchor 330 to secure the pad 310 to the patient's shoulder.

Figure 4:
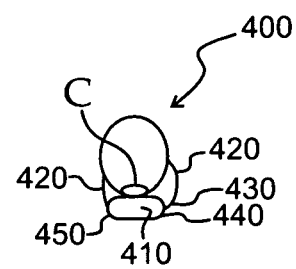
FIG. 4 illustrates an embodiment of an improved wound care system, constructed in accordance with the principles herein, wherein the improved wound care system is securely attached via a fastener and an anchor to an elbow of a patient.

Another embodiment of a system shown generally at 400 in FIG. 4 includes a device 410 secured to an elbow, indicated at C of a patient, via fastener 420, wherein the fastener 420 is wrapped around an arm of the patient. The fastener 420 is selectively secured to an anchor 430, provided at a first end 440 of the device 410, while the fastener 420 is secured to a second end 450 of the device 410.

Figure 5:
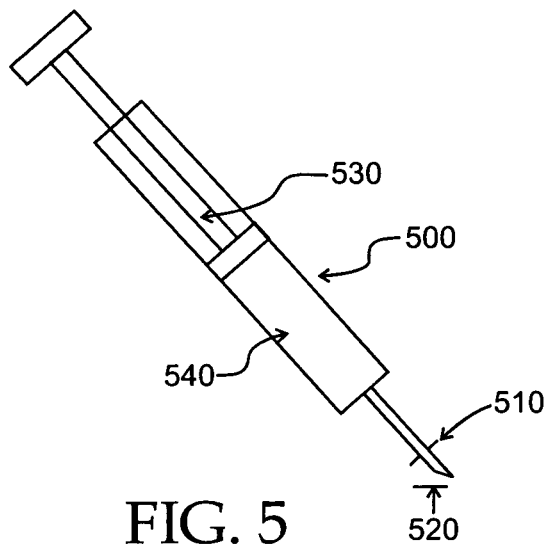
FIG. 5 illustrates a medicinal delivery device of an embodiment of an improved wound care system, constructed in accordance with the principles herein.

As illustrated in FIG. 5, a medicinal delivery device, shown generally at 500 is provided. The medicinal delivery device 500 can be formed of a suitable delivery mechanism, and can, for example, take the form of a simple syringe, as is commonly found in medical practice, but with the addition of a material stop 510 approximately 10 millimeters from an end 520 of the delivery device 500. Significantly, the end 520 does not need to have unduly sharp points, since it is only needed to puncture thin, flexible material, such as a plastic material.

The delivery device 500 can be loaded by inserting the end 520 into a medicine and drawing up a plunger 530, so as to draw the medicine into a body 540 of the delivery device 500. The delivery device 500 allows for the cost effective application of any of the wide variety of medicines or chemicals (e.g. silver) used to treat patients with wounds, such as pressure ulcers, and the size of the end 520 can be adjusted to accommodate delivery of different materials having differing flow rates.

Figure 6:
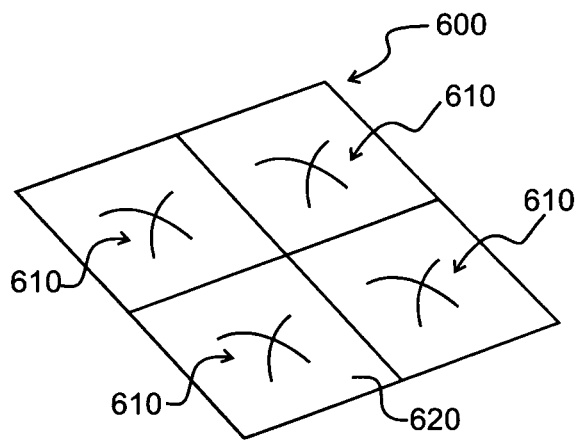
FIG. 6 illustrates target bubbles to be treated using the medicinal delivery system of FIG. 5 of an improved wound care system, constructed in accordance with the principles herein.

As illustrated in FIG. 6, a treatment area of a device, such as the devices 110, 310, 410, or any other suitable device, can be determined by a healthcare professional, and marked with x's 610, shown on an inside, bubble surface of a device 600. The health care giver uses the wound care device to identify the area of concern to be treated and before "activating" the bubbles at x's 610 to be used to protect the area, the medicinal delivery device 500 of FIG. 5 is used to apply the treatment in the area of concern by inserting the delivery device 500 into the x's 610 until it reached the stop 510. The medicine is then inserted into the device by depressing the plunger 530. In this manner, the healthcare professional using the medicinal delivery device 500 can fill it with the appropriate quantity of the prescribed substance, and deliver it to a designated treatment area of the device. This allows the best treatment to be used and is cost effective. The healthcare provider can repeatedly fill and insert the device into the x's 610 until the entire designated treatment area is filled with medicine or a suitable treating substance. Once all the bubbles to be activated are filled via the x's 610 with the treatment material, the same delivery device 500 can be used to activate the bubbles that will cover the area of concern by punching through the bubble material with the stop 510 and rupturing a plastic surface 620. Now the treatment material is available to come in contact with a wound and provide treatment, when the wound care device is secured to the patient via the fastener and anchor.

The medicinal delivery device 500 includes of the body 540, the plunger 530, the stop 510 and an insertion point, tip, or end 520. Each component of the delivery device 500 can be made of various materials to include plastic, glass, metal or other suitable materials.

The improved wound care treatment device shown generally at 100, 200, 300, 400, and 700, or any other suitable device, is affixed to maximize treatment by suspending and removing pressure while delivering appropriate medical treatment, where desired or needed. As a wound treated in accordance with the principles herein heals, the process is repeated as the area of concern diminishes in size until the patient no longer needs treatment.

Figure 7:
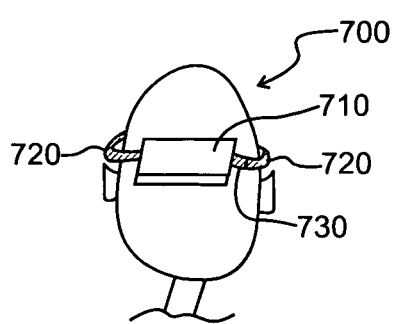
FIG. 7 illustrates an embodiment of an improved wound care system, constructed in accordance with the principles herein, wherein the improved wound care system is securely attached via a fastener and an anchor to a head of a patient

Another embodiment of a wound care system constructed in accordance with the principles herein is illustrated generally at 700 in FIG. 7. The system includes a suitable device 710 attached to the head of a patient via a fastener 720 wrapped around the head of the patient and secured at an anchor 730.

The improved wound care system disclosed herein is intended to maximize the wound healing of a patient by providing environmental and medicinal factors that improve the condition of the treated site. It is contemplated that proper use of the system herein will reduce the duration of hospitalizations arising from wound development and associated infection and/or illness.

Although example implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

I claim as my invention:

1. A method for treating a wound on a patient with a wound care system, the method comprising the following steps: providing a wound care device having a treatment area with an inside treatment surface configured to contact a wound, a bubble surface formed on the treatment area, and a plurality of bubbles formed on the bubble surface, each of the plurality of bubbles being adapted and constructed to selectively and refillably receive treatment material, providing at least one medicinal delivery device, the at least one medicinal delivery device being configured to individually fill selective ones of the plurality of bubbles on the bubble surface of the treatment area, loading the at least one medicinal delivery device with a treatment material, using the at least one medicinal delivery device to selectively fill, through the inside treatment surface, at least one of the plurality of bubbles with the treatment material; activating at least one of the plurality of bubbles filled with the treatment material using the at least one medicinal delivery device by punching through the at least one of the plurality of bubbles until a stop of the at least one medicinal delivery device contacts the bubble surface of the at least one of the plurality of bubbles, and securing the wound care device to a wounded area of the patient.

2. A method for treating a wound on a patient with a wound care system, the method comprising the following steps: providing a wound care device having a treatment area with an inside treatment surface configured to contact a wound, a bubble surface formed on the treatment area, and a plurality of bubbles formed on the bubble surface, each of the plurality of bubbles being adapted and constructed to selectively and refillably receive treatment material; providing at least one medicinal delivery device, the at least one medicinal delivery device being configured to individually fill selective ones of the plurality of bubbles on the bubble surface of the treatment area, the at least one medicinal delivery device comprising a body; a depressible plunger mounted in the body; a stop; and an insertion point extending from the body; loading the at least one medicinal delivery device with the treatment material; using the at least one medicinal delivery device to selectively fill, through the inside treatment surface, at least one of the plurality of bubbles with the treatment material, the method further comprising: inserting the insertion point of the at least one medicinal delivery device systematically into a selected at least one of the plurality of bubbles to be filled until the stop reaches the the bubble surface of the selected at least one of the plurality of bubbles of the wound care device such that an end of the insertion point is within the selected at least one of the plurality of bubbles; and depressing the plunger until the selected at least one of the plurality of bubbles is filled; activating the at least one of the plurality of bubbles filled with the treatment material using the at least one medicinal delivery device by punching through the at least one of the plurality of bubbles until a stop of the at least one medicinal delivery device contacts the bubble surface of the at least one of the plurality of bubbles; and securing the wound care device to a wounded area of the patient.

3. A method for treating a wound on a patient with a wound care system, the method comprising the following steps: providing a wound care device having a treatment area with an inside treatment surface configured to contact a wound, a bubble surface formed on the treatment area, and a plurality of bubbles formed on the bubble surface, each of the plurality of bubbles being adapted and constructed to selectively and refillably receive treatment material; providing at least one medicinal delivery device, the at least one medicinal delivery device being configured to individually fill selective ones of the plurality of bubbles on the bubble surface of the treatment area; loading the at least one medicinal delivery device with the treatment material; identifying on the inside treatment surface an area of concern corresponding to the wound; using the at least one medicinal delivery device to selectively fill, through the inside treatment surface, at least one of the plurality of bubbles within the identified area of concern with the treatment material; activating the at least one of the plurality of bubbles filled with the treatment material using the at least one medicinal delivery device by punching through the at least one of the plurality of bubbles until a stop of the at least one medicinal delivery device contacts the bubble surface of the at least one of the plurality of bubbles; and securing the wound care device to a wounded area of the patient.

4. The method in accordance with claim 3, further comprising securing the wound care device to the patient with the identified area of concern with the wound.

\* \* \* \* \*